United States Patent
Lassalle et al.

(10) Patent No.: US 7,473,564 B2
(45) Date of Patent: Jan. 6, 2009

(54) KIT AND METHOD FOR DETECTING THE ESM-1 PROTEIN

(75) Inventors: Philipp Lassalle, Lille (FR); David Bechard, Paris (FR); André-Bernard Tonnel, Premesques (FR)

(73) Assignees: Institut Pasteur de Lille, Paris (FR); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 10/416,204

(22) PCT Filed: Nov. 8, 2001

(86) PCT No.: PCT/FR01/03477

§ 371 (c)(1),
(2), (4) Date: Oct. 21, 2003

(87) PCT Pub. No.: WO02/39123

PCT Pub. Date: May 16, 2002

(65) Prior Publication Data

US 2004/0063164 A1      Apr. 1, 2004

(30) Foreign Application Priority Data

Nov. 9, 2000    (FR)    .................. 00 14421

(51) Int. Cl.
| | |
|---|---|
| C07K 16/18 | (2006.01) |
| C12N 5/20 | (2006.01) |
| G01N 33/53 | (2006.01) |
| G01N 33/543 | (2006.01) |
| G01N 33/577 | (2006.01) |
| C12P 21/08 | (2006.01) |
| G01N 33/574 | (2006.01) |

(52) U.S. Cl. ............. 436/518; 435/7.1; 435/7.5; 435/7.94; 435/70.21; 435/452; 435/331; 435/332; 435/334; 435/975; 436/547; 436/548; 436/811; 436/813; 530/387.9; 530/388.2; 530/388.22; 530/389.1; 530/391.1

(58) Field of Classification Search .............. 435/7.1, 435/7.5, 7.94, 70.21, 452, 331, 332, 334, 435/975; 436/518, 547, 548, 64, 811, 813; 530/387.9, 388.2, 388.22, 389.1, 391.1

See application file for complete search history.

(56) References Cited

U.S. PATENT DOCUMENTS

| | | | | |
|---|---|---|---|---|
| 5,506,111 | A | * | 4/1996 | Hosoda et al. ............. 435/7.94 |
| 5,747,280 | A | | 5/1998 | Hastings et al. |
| 6,670,328 | B1 | * | 12/2003 | Lassalle et al. ............... 514/12 |

FOREIGN PATENT DOCUMENTS

| | | | |
|---|---|---|---|
| WO | WO 96 17931 | | 6/1996 |
| WO | 99/45028 | * | 9/1999 |

OTHER PUBLICATIONS

Hellstrom et al., 1985. In Monoclonal Antibodies for Cancer Detection and Therapy (Balwin et al, eds.), Academic Press, London, p. 20.*

Harlow et al., 1988. Antibodies. A Laboratory Manual, Cold Spring Harbor Laboratory, Cold Spring Harbor. pp. 72-77.*

Walter et al., 1980. Antibodies specific for the carboxy- and amino-terminal regions of simian virus 40 large tumor antigen. Proc. Natl. Acad. Sci. USA 77: 5197-5200.*

International Search Report in corresponding PCT/FR01/03477.

Bechard et al.; Characterization of the secreted form of endothelial-cell-specific molecule 1 by specific monoclonal antibodies; J. Vasc. Res. (2000) 37:417-425.

Lassalle et al.; ESM-1 is a novel human endothelial cell-specific molecule expressed in lung and regulated by cytokines; J. Biol. Chem. (1996) vol. 271, No. 34 pp. 20458-20464.

International Search Report in PCT/FR01/03475.

Hendrix et al., Expression of select-endothelial-specific genes by aggressive human melanoma cells: Putative role of VE-Cadherin (CD144) in vasculogenic mimicry; FASEB Journal, vol. 15, No. 5 (2001) p. A743 XP001015835.

* cited by examiner

Primary Examiner—Long V. Le

*Assistant Examiner*—James L Grun
(74) *Attorney, Agent, or Firm*—Finnegan, Henderson, Farabow, Garrett & Dunner, L.L.P.

(57) ABSTRACT

The invention concerns a kit for the detection of protein ESM-1 in a sample, comprising:
  a) a first antibody specifically binding to the N-terminal region of protein ESM-1 contained between the amino acid in position 20 and the amino acid in position 78 of the amino acid sequence of this protein; and
  b) a second antibody specifically binding to the C-terminal region contained between the amino acid in position 79 and the amino acid in position 184 of the amino acid sequence of protein ESM-1.

17 Claims, 8 Drawing Sheets

FIGURE 2 A, B, C

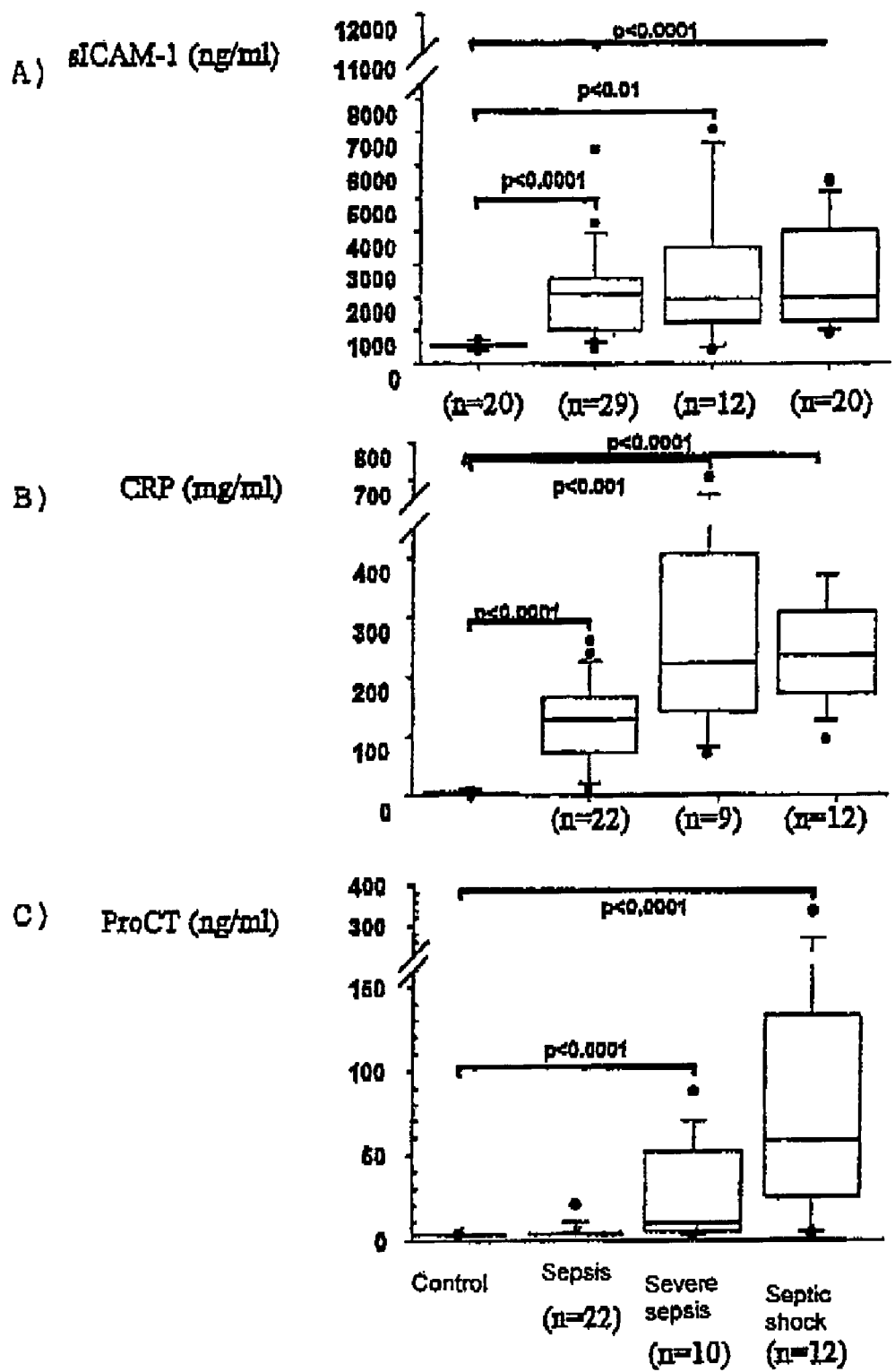
FIGURE 5 A, B, C

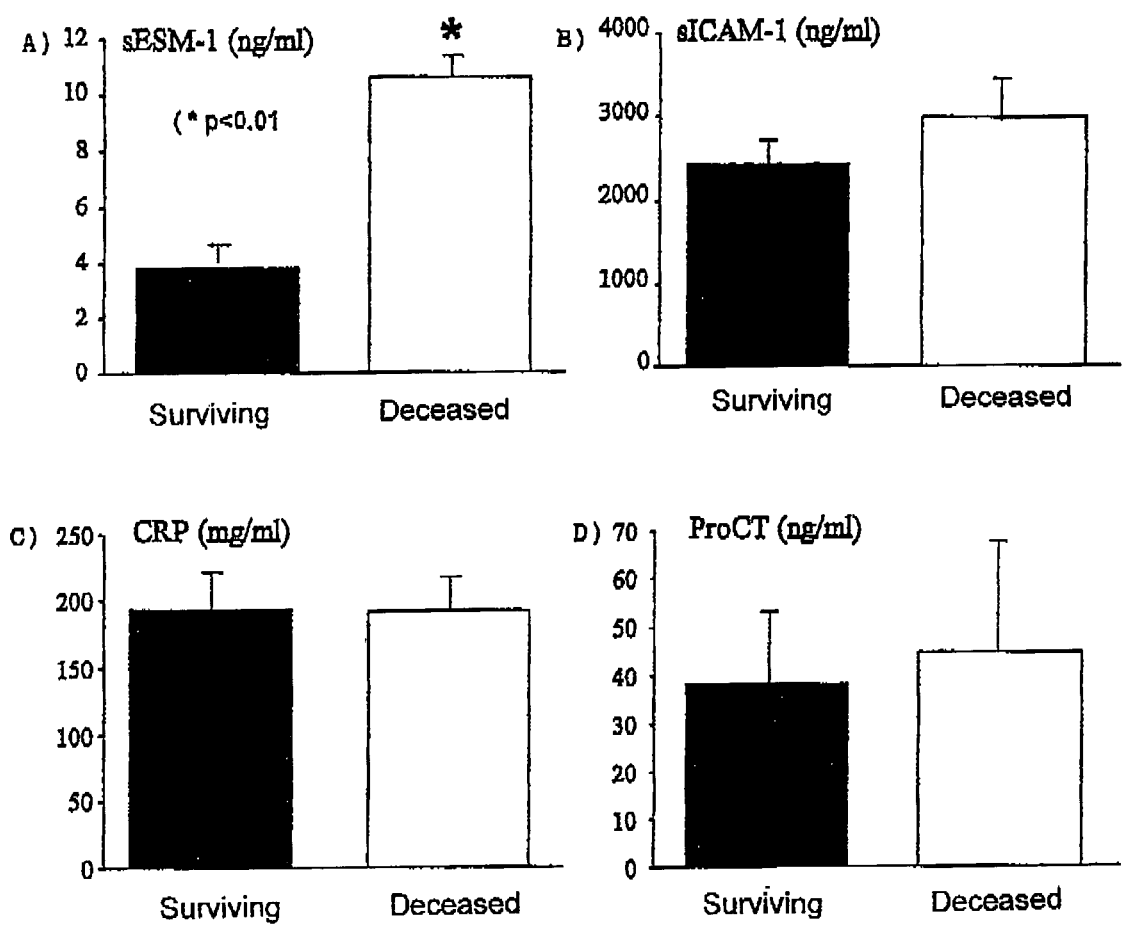
FIGURE 6 A, B, C, D

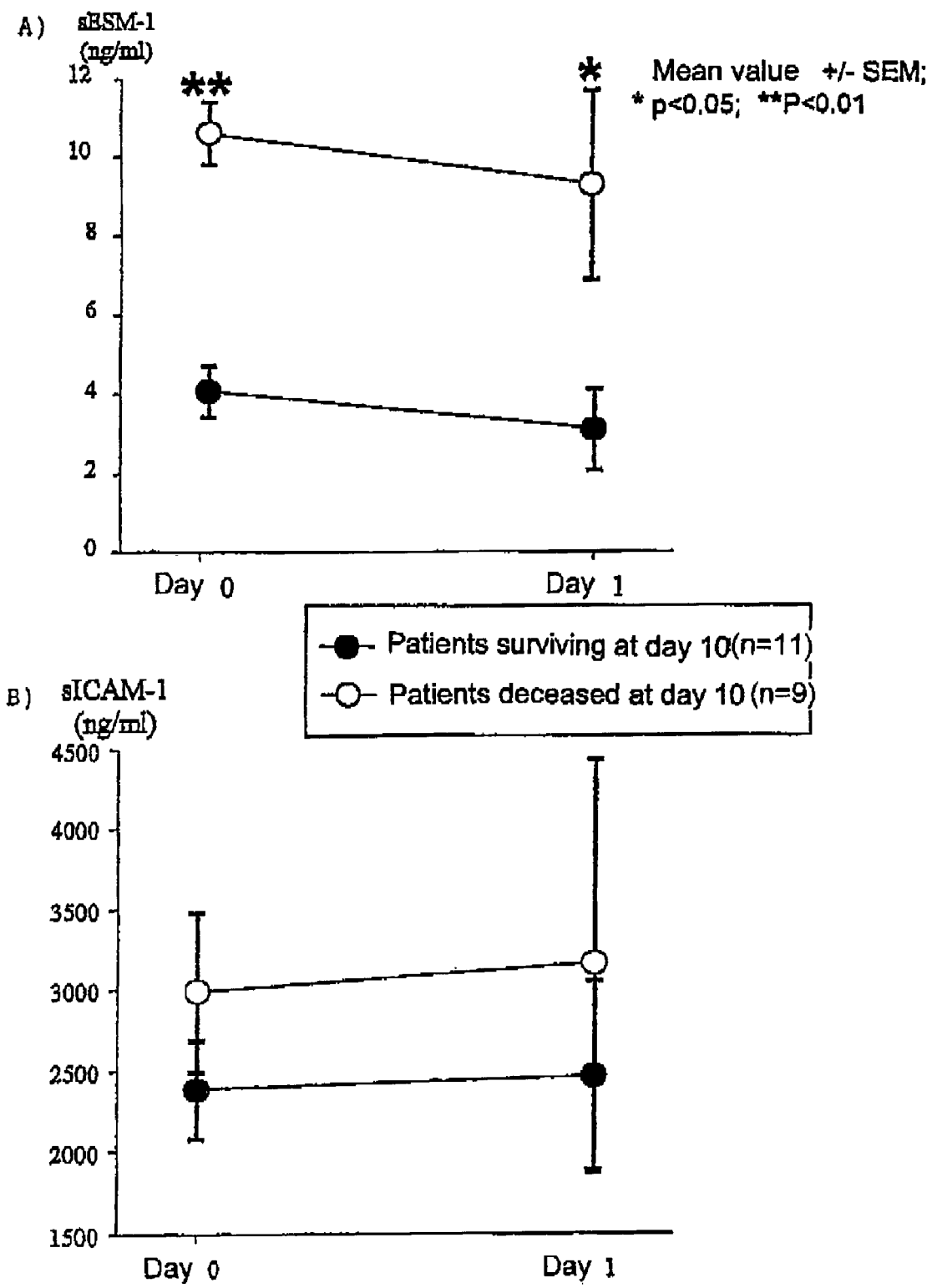
FIGURE 7 A, B

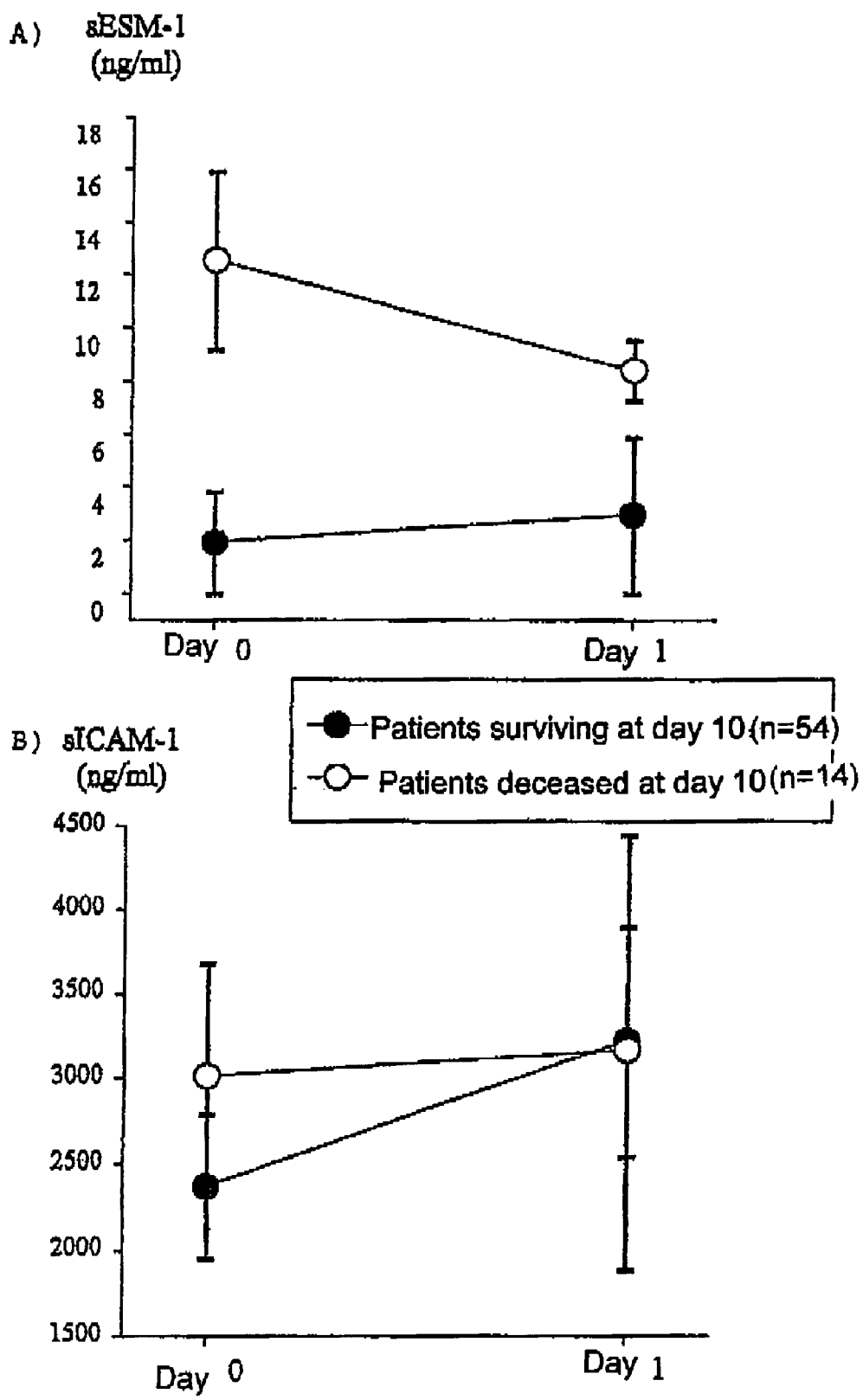
FIGURE 8 A, B

SEQUENCE LISTING

<160> NUMBER OF SEQ ID NOS: 2

<210> SEQ ID NO 1
<211> LENGTH: 184
<212> TYPE: PRT
<213> ORGANISM: Homo sapiens

<400> SEQUENCE: 1

Met Lys Ser Val Leu Leu Thr Thr Leu Leu Val Pro Ala His Leu
1               5                   10                  15

Val Ala Ala Trp Ser Asn Asn Tyr Ala Val Asp Cys Pro Gln His Cys
            20                  25                  30

Asp Ser Ser Glu Cys Lys Ser Ser Pro Arg Cys Lys Arg Thr Val Leu
            35                  40                  45

Asp Asp Cys Gly Cys Cys Arg Val Cys Ala Ala Gly Arg Gly Glu Thr
        50                  55                  60

Cys Tyr Arg Thr Val Ser Gly Met Asp Gly Met Lys Cys Gly Pro Gly
65                  70                  75                  80

Leu Arg Cys Gln Pro Ser Asn Gly Glu Asp Pro Phe Gly Glu Glu Phe
                85                  90                  95

Gly Ile Cys Lys Asp Cys Pro Tyr Gly Thr Phe Gly Met Asp Cys Arg
            100                 105                 110

Glu Thr Cys Asn Cys Gln Ser Gly Ile Cys Asp Arg Gly Thr Gly Lys
        115                 120                 125

Cys Leu Lys Phe Pro Phe Phe Gln Tyr Ser Val Thr Lys Ser Ser Asn
130                 135                 140

Arg Phe Val Ser Leu Thr Glu His Asp Met Ala Ser Gly Asp Gly Asn
145                 150                 155                 160

Ile Val Arg Glu Glu Val Val Lys Glu Asn Ala Ala Gly Ser Pro Val
                165                 170                 175

Met Arg Lys Trp Leu Asn Pro Arg
            180

<210> SEQ ID NO 2
<211> LENGTH: 2006
<212> TYPE: DNA
<213> ORGANISM: Homo sapiens

<400> SEQUENCE: 2
cttcccacca gcaaagacca cgactggaga gccgagccgg aggcagctgg gaaacatgaa      60
gagcgtcttg ctgctgacca cgctcctcgt gcctgcacac ctggtggccg cctggagcaa     120
taattatgcg gtggactgcc ctcaacactg tgacagcagt gagtgcaaaa gcagcccgcg     180
ctgcaagagg acagtgctcg acgactgtgg ctgctgccga gtgtgcgctg cagggcgggg     240
agaaacttgc taccgcacag tctcaggcat ggatggcatg aagtgtggcc cggggctgag     300
gtgtcagcct tctaatgggg aggatccttt tggtgaagag tttggtatct gcaaagactg     360
tccctacggc accttcggga tggattgcag agagacctgc aactgccagt caggcatctg     420 tgacagggg acgggaaaat gcctgaaatt ccccttcttc caatattcag taaccaagtc     480
ttccaacaga tttgtttctc tcacggagca tgacatggca tctggagatg caatattgt     540 gagagaagaa gttgtgaaag agaatgctgc cgggtctccc gtaatgagga aatggttaaa     600
tccacgctga tcccggctgt gatttctgag agaaggctct attttcgtga ttgttcaaca     660
cacagccaac attttaggaa ctttctagat atagcataag tacatgtaat ttttgaagat     720

```
ccaaattgtg atgcatggtg gatccagaaa acaaaaagta ggatacttac aatccataac     780
atccatatga ctgaacactt gtatgtgttt gttaaatatt cgaatgcatg tagatttgtt     840
aaatgtgtgt gtatagtaac actgaagaac taaaaatgca atttaggtaa tcttacatgg     900
agacaggtca accaaagagg gagctaggca aagctgaaga ccgcagtgag tcaaattagt     960
tctttgactt tgatgtacat taatgttggg atatggaatg aagacttaag agcaggagaa    1020
gatggggagg gggtgggagt gggaaataaa atatttagcc cttccttggt aggtagcttc    1080
tctagaattt aattgtgctt ttttttttttt tttggctttg ggaaaagtca aaataaaaca    1140
accagaaaac ccctgaagga agtaagatgt ttgaagctta tggaaatttg agtaacaaac    1200
agctttgaac tgagagcaat ttcaaaaggc tgctgatgta gttcccgggt tacctgtatc    1260
tgaaggacgg ttctggggca taggaaacac atacacttcc ataaatagct ttaacgtatg    1320
ccacctcaga gataaatcta agaagtattt tacccactgg tggtttgtgt gtgtatgaag    1380
gtaaatattt atatattttt ataaataaat gtgttagtgc aagtcatctt ccctacccat    1440
atttatcatc ctcttgagga aagaaatcta gtattatttg ttgaaaatgg ttagaataaa    1500
aacctatgac tctataaggt tttcaaacat ctgaggcatg ataaatttat tatccataat    1560
tataggagtc actctggatt tcaaaaaatg tcaaaaaatg agcaacagag ggaccttatt    1620
taaacataag tgctgtgact tcggtgaatt ttcaatttaa ggtatgaaaa taagtttta    1680 ggaggtttgt aaaagaagaa tcaattttca gcagaaaaca tgtcaacttt aaaatatagg    1740
tggaattagg agtatatttg aaagaatctt agcacaaaca ggactgttgt actagatgtt    1800
cttaggaaat atctcagaag tattttattt gaagtgaaga acttatttaa gaattatttc    1860
agtatttacc tgtattttat tcttgaagtt ggccaacaga gttgtgaatg tgtgtggaag    1920
gcctttgaat gtaaagctgc ataagctgtt aggttttgtt ttaaaaggac atgtttatta    1980
ttgttcaata aaaaagaaca agatac                                         2006
```

KIT AND METHOD FOR DETECTING THE ESM-1 PROTEIN

This application is a 35 U.S.C. § 371 filing of PCT/FR01/03477, filed Nov. 8, 2001, which is based on and claims the benefit of French application FR 00/14421, filed Nov. 9, 2000. The entire disclosures of these applications are relied upon and incorporated by reference herein.

SCOPE OF THE INVENTION

The present invention concerns a kit for detecting protein ESM-1 in a sample. It also relates to a method for detecting protein ESM-1 in a sample using such a kit.

The kit and the detection method for protein ESM-1 according to the invention are industrially applicable particularly for quantification of protein ESM-1 in biological samples, and especially biological samples from patients for whom a deterioration of the endothelial vascular walls is suspected.

STATE OF THE ART

Protein ESM-1 (for "Endothelial-cell-Specific Molecule 1") is a protein mainly expressed by the endothelial cells, and predominantly by the vascular endothelial cells. Protein ESM-1 was described for the first time by LASSALLE et al. (1996). The messenger RNA of ESM-1 codes for a polypeptide of 184 amino acids whose sequence is described in FIG. 1 of the article by LASSALLE et al. (1996).

Protein ESM-1 isolated from the cell lysates of human endothelial cells has an apparent molecular weight of 20 kDa. The secreted form of protein ESM-1 has an apparent molecular weight of 50 kDa, indicating that the secreted protein ESM-1 has undergone post-translational modifications.

The use of monoclonal antibodies to detect protein ESM-1 is disclosed in the French patent application published under the number n°2.775.691 and in the article by BECHARD et al. (2000). These monoclonal antibodies were prepared by immunization of mice with an antigen composed of the sequence running from the amino acid in position 79 up to the amino acid in position 184 of protein ESM-1 which had been fused with protein GST (glutathione-S-transferase). Three families of monoclonal antibodies had been characterized, these antibody families fixing respectively to the antigenic determinants AgD1 79P-99C (antibodies MEP 01, MEP 06 and MEP 21), AgD2 119 S-139V (antibodies MEP 08 and MEP13) and AgD3 159G-184R (antibodies MEP 04, MEP 14 and MEP19).

BECHARD et al. (2000) described the development of an immunoenzymatic test of the "sandwich" type using the monoclonal antibodies MEP 19 and MEP 21 to perform a test for detecting protein ESM-1 in a sample. This test allowed the authors to demonstrate strong production of protein ESM-1 in the serum of patients hospitalized for septic shock. The results presented in FIG. 4 of this article show that the detection test using the antibodies MEP 19 and MEP 21 enables a concentration of protein ESM-1 above 4 nanograms per milliliter to be detected.

However, although the immunoenzymatic test for protein ESM-1 described by BECHARD et al. (2000) is suitable for high concentrations of protein ESM-1 in a sample, it does not detect low quantities of this protein, which are however significant in physiological disorders, such as a deterioration of the endothelial cell wall in patients, as is shown according to the invention.

SUMMARY OF THE INVENTION

The applicant has endeavoured to develop an immunological test for the detection of protein ESM-1 in a sample which is much more sensitive than the test described in the state of the art.

The object of the invention is a kit for the detection of protein ESM-1 in a sample, comprising:

a) a first antibody facing specifically to the N-terminal region contained between the amino acid in position 1 and the amino acid in position 78 of the amino acid sequence of protein ESM-1; and b) a second antibody fixing specifically to the C-terminal region contained between the amino acid in position 79 and the amino acid in position 184 of the amino acid sequence of protein ESM-1.

A further object of the invention is a method for detecting protein ESM-1 in a sample, characterized in that it comprises the following steps:

a) placing the sample to be tested in contact with a support on which is immobilized a first antibody fixing specifically to the N-terminal region or the C-terminal region of the amino acid sequence of protein ESM-1;

b) placing the complex potentially formed between the immobilized antibody and protein ESM-1 in contact with a second antibody fixing specifically to the N-terminal region or the C-terminal region not recognized by the first antibody; and c) detecting the complex potentially formed between protein ESM-1 and the second antibody.

The invention also concerns certain antibodies used in the above method.

A further object of the invention is the use of the detection kit according to the invention for detecting a deterioration of the endothelial vascular wall in a patient, particularly in a patient suffering from septic shock or cancer or a patient undergoing a therapeutic treatment likely to be cytotoxic against vascular endothelial cells.

DETAILED DESCRIPTION OF THE INVENTION

Detection Kit According to the Invention

The detection kit according to the invention enables the presence of protein ESM-1 to be detected in a sample with high sensitivity.

The sample in which the presence of protein ESM-1 is sought may be of any type. It is preferably a biological fluid such as serum, plasma, whole blood, urine, cerebrospinal fluid, or culture supernatants or cell lysates.

The applicant has shown that protein ESM-1 secreted by eukaryotic cells has specific properties which are not found in protein ESM1 produced by prokaryotic cells, such as cells of *Escherichia coli*.

Protein ESM-1 is secreted by eukaryotic cells, and particularly by endothelial cells, in the form of a glycoprotein, more precisely a proteoglycan having a chain of the chondroitin/d rmatan sulfat type. In addition, the applicant has shown that protein ESM-1 secreted by eukaryotic cells undergoes other post-translational modifications including conformational modifications caused by the formation of disulfide bridges between the cysteine residues of the N-terminal region of this protein. The polypeptide ESM-1 of 184 amino acids is referenced as sequence SEQ ID N°1.

In order to develop a highly sensitive immunological detection test for protein ESM-1, the applicant has pursued the strategy of preparing monoclonal antibodies directed against the N-terminal region running from the amino acid in position 20 to the amino acid in position 78 of the sequence SEQ ID N°1 described by LASSALLE et al. (1996), the amino acid in position 20 constituting the amino-terminal amino acid of the secreted protein ESM-1.

The monoclonal antibodies prepared by the applicant are preferably directed against the protein ESM-1 secreted by eukaryotic cells and having undergone the post-translational modifications mentioned above.

More specifically, the applicant has produced cell lines of hybridomas producing monoclonal antibodies fixing specifically to the region of protein ESM-1 undergoing conformational modifications arising from the creation of disulfide bridges, in other words antibodies directed against the N-terminal region of protein ESM-1 running from the amino acid in position 20 up to the amino acid in position 78 of the amino acid sequence of protein ESM-1 of sequence SEQ ID N°1.

In order to obtain a tool for detecting protein ESM-1 in a sample, the applicant has developed an immunological test of the "sandwich" type using two antibodies specifically binding to two distinct regions of protein ESM-1, respectively an antibody binding specifically to the N-terminal region running from the amino acid in position 20 up to the amino acid in position 78 of ESM-1 and an antibody binding specifically to the C-terminal region running from position 79 to position 184 of the sequence of ESM-1.

A first object of the invention thus consists of a kit for detecting protein ESM-1 in a sample, said kit comprising:

a) a first antibody binding specifically to the N-terminal region of protein ESM-1 contained between the amino acid in position 20 and the amino acid in position 78 of the amino acid sequence of this protein; and b) a second antibody specifically binding to the C-terminal region contained between the amino acid in position 79 and the amino acid in position 184 of the amino acid sequence of protein ESM-1.

The antibody binding specifically to the N-terminal region of ESM-1 is preferably directed specifically against the N-terminal region of protein ESM-1 secreted by eukaryotic cells and having undergone the post-translational modifications detailed above. This means that the antibody binding specifically to the N-terminal region has been obtained according to a method including a step in which an animal has been injected with a purified preparation of protein ESM-1 produced by a eukaryotic cell.

"Antibody," in the context of the invention, should be understood to be a molecule containing a "paratope" able to bind specifically to the N-terminal region or to the C-terminal region of protein ESM-1. "Antibody," according to the invention, should be understood also as a homogeneous population of molecules all containing the same "paratope" able to bind specifically to the N-terminal region or to the C-terminal region of protein ESM-1.

"Paratope" should be understood as the antigenic combination site contained in the Fab fragment of an antibody, which is localized in the hypervariable or CDR domains of the variable domains $V_H$ and $V_L$ of the heavy chain or the light chain of an immunoglobulin.

An antibody according to the invention may be prepared from hybridomas according to the technique described by KOHLER and MIELSTEIN (1975), or by the technique of the hybridoma of human B cells described by KOZBOR (1983). An antibody according to the invention also includes the fragments of single chain Fv chimeric antibodies (ScFv for "Single Chain Fv") such as disclosed in the U.S. Pat. No. 64.946.778 and by MARTINEAU et al. (1998). An antibody according to the invention may also be produced by the phage banks ("Phage Display Libraries") such as those described by RIDDER et al. (1995). An antibody according to the invention may also be a human antibody produced according to the technique described by REINMANN et al. (1997) or by the technique described by LEGER et al. (1997).

The detection kit for protein ESM-1 according to the invention preferably comprises one of the two antibodies immobilized on a support. In this preferred embodiment, the detection kit is presented in a "ready to use" form to perform an immunodetection test of the "sandwich" type for protein ESM-1.

It has been shown according to the invention that the use of a kit such as defined above for the detection of the presence of protein ESM-1 in a sample results in a detection sensitivity 10 times greater than that observed with the test for detection of ESM-1 described by BECHARD et al. (2000).

The high sensitivity of the immunodetection test according to the invention has made it possible to detect very low concentrations of protein ESM-1 in a biological sample, for example in human serum, and has thus allowed early detection of the deterioration of the endothelial vascular walls in a patient.

In particular, the use of an immunodetection kit according to the invention has enabled serum concentrations of ESM-1 of from 1 to 3 nanograms per ml to be detected in "atopic" individuals suffering from sepsis.

As is shown in the examples, the use of an immunodetection kit according to the invention can be used to detect concentrations of ESM-1 of the order of 100 to 200 picogram/ml, while the test described by BECHARD et al. (2000) does not detect concentrations of ESM-1 of less than 1 nanogram/ml.

The antibody directed against the N-terminal region of ESM-1 is advantageously a monoclonal antibody produced by a hybridoma line obtained after immunization of a mammal, preferably a mouse, with recombinant protein ESM-1 synthesized by a eukaryotic cell, for example a cell of the CHO line transformed by an expression vector containing a DNA insert coding for protein ESM-1 described by LASSALLE et al., for example the vector pcDNA3.

It is preferably the monoclonal antibody produced by the hybridoma line designated MEC 15 deposited at the Collection de Cultures de Micro-organismes (CNCM) of the Institut Pasteur, located at Institut Pasteur, 28 rue du Docteur Roux, F-75724 Paris Cedex 15, France, on 17 Oct. 2000 under the access number I-2572.

The MEC15 antibody constitutes an object of the invention.

The antibody binding specifically to the C-terminal part of the protein ESM-1 may be either an antibody directed against protein ESM-1 produced by a prokaryotic cell, such as *Escherichia coli*, or by a eukaryotic cell, such as cells of the CHO line.

The antibody binding specifically to the C-terminal part of the protein ESM-1 is preferably chosen from among the antibodies able to recognize one of the three following antigenic determinants of protein ESM-1:

the determinant AgD1 running from the proline residue in position 79 up to the cysteine residue in position 99 of ESM-1, such as the antibodies produced by the hybridoma lines MEP01, MEP06 and MEP21 described by BECHARD et al. (2000);

the antigenic determinant AgD2 running from the serine residue in position 119 up to the valine residue in position 139 of ESM-1 recognized by the antibodies produced by the hybridomas MEP08 and MEP13 described by BECHARD et al. (2000);

the antigenic determinant AgD3 running from the glycine residue in position 159 up to the arginine residue in position 184 of ESM-1 is recognized by the antibodies produced by the hybridoma lines MEP04, MEP14 and MEP19 described by BECHARD et al. (2000).

In a preferred embodiment, a person skilled in the art may advantageously refer, for the use of an antibody specifically binding to the C-terminal region of protein ESM-1, to the following antibodies:

the specific monoclonal antibodies of the antigenic determinant D1 produced by the hybridoma line deposited at the CNCM on 19 Nov. 1997 under the access number I-1944 (antibody MEP 21);

the specific monoclonal antibodies of the antigenic determinant D2 produced by the hybridoma line deposited at the CNCM on 19 Nov. 1997 under the access number I-1941 (antibody MEP08);

the specific monoclonal antibodies of the antigenic determinant D3 produced by the hybridoma line deposited at the CNCM on 19 Nov. 1997 under the access numbers I-1942 (antibody MEP14) and I-1943 (antibody MEP19).

In the preferred embodiment of the immunodetection kit according to the invention, the first and the second antibodies are chosen so that their respective recognition sites on the protein ESM-1 are very distant from each other in order to avoid any occurrence of competitive fixation of one antibody with respect to the other on the protein, which could be caused by a steric hindrance phenomenon in the case where the respective recognition sites of the two antibodies are too close.

Thus, in a preferred embodiment of a detection kit according to the invention, the first antibody specifically binding to the N-terminal region of protein ESM-1 is the antibody produced by the hybridoma line MEC15. According to this preferred embodiment, the antibody specifically binding to the C-terminal region of protein ESM-1 is the monoclonal antibody produced by the hybridoma line MEP14.

In general, an antibody directed against the C-terminal region of protein ESM-1 may be selected according to the technique described by BECHARD et al. (2000), which consists of preparing an expression vector containing a DNA insert coding for the C-terminal region of protein ESM-1 fused to the protein GST, then to immunize mice with purified protein ESM-1 obtained from cell lysates of *Escherichia coli* cells transformed with the said expression vector. After fusion of mouse spleen cells thus immunized with myeloma cells in order to obtain a series of hybridomas producing monoclonal antibodies, the antibodies of interest binding specifically to the C-terminal region of protein ESM-1 may be selected by mapping the epitopes using peptides derived from ESM-1 containing progressive deletions of the N-terminal end of the C-terminal region of this protein.

Similarly, a skilled person may select the antibodies specifically binding to the N-terminal region of protein ESM-1 by immunizing mice with whole protein ESM-1, preferably whole protein ESM-1 produced by a eukaryotic host cell, then by producing a series of hybridoma lines from the spleen cells of the immunized mice, then by selecting the antibodies of interest specifically binding to the N-terminal region, for example, by competitive immunodetection tests with the antibodies specifically fixing to the C-terminal region of ESM-1. The antibodies of interest are those that do not compete with the specific antibodies of the C-terminal region of ESM-1, in other words the antibodies that do not compete with the specific antibodies of the antigenic determinants D1, D2, and D3 of protein ESM-1.

One of the two antibodies comprising the detection kit according to the invention is preferably immobilized on a support. The support on which the antibody is immobilized may be of any type known to a person skilled in the art specializing in immunodetection tests, in particular in immunodetection tests of the "sandwich" type.

As an illustration, the support on which the antibody is immobilized may be a porous or non-porous material insoluble in water. The support may be hydrophilic and contain inorganic powders such as silica, magnesium and aluminium sulfate, natural polymers, in particular cellulose materials and their derivatives, natural or synthetic polymers such as nitro-cellulose, cellulose acetate, poly(vinyl chloride), polyacrylamide, crosslinked dextran, agarose, polyacrylate, polyethylene, polypropylene, poly(4-methylbutene), polystyrene, polymethacrylate, poly(ethylene terephthalate), Nylon, poly(vinyl butyrate), certain types of glass such as Bioglass, or ceramics.

The fixation of an antibody according to the invention onto a support may be performed by techniques well known to a skilled person. The support may be in various different forms, including strips or in particular beads. The surface of the support may be polyfunctional or able to be polyfunctionalized so as to fix the antibody via covalent or non-covalent interactions which may be specific or non-specific. As an illustration, for the immobilization of an antibody onto a support, a person skilled in the art may advantageously refer to the U.S. Pat. No. 4,168,146 or the U.S. Pat. No. 4,347,311.

One of the antibodies comprising the detection kit is advantageously covalently bound to a molecule enabling its direct or indirect detection.

In the embodiment in which the antibody is immobilized on a support, the other antibody is preferably covalently bound to a molecule enabling its direct or indirect detection.

The detectable molecule may be isotopic or non-isotopic.

As an illustrative but non-limiting example, the detectable molecule may be involved in a catalytic reaction, such as an enzyme, an enzyme fragment, an enzyme substrate, an enzyme inhibitor, a coenzyme or a catalyst. The detectable molecule may also be a chromogen, such as a fluorophore, a colorant, or a chemiluminescent molecule.

The detectable molecule may thus be a fluorescent molecule such as the molecules described by ICHINOSE at al. (1991) or the fluorescent isothiocyanate derivatives, phycoerithrine, rhodamine isothiocyanate, dansyl chloride or the compound XRITC, protein GFP ("Green Fluorescent Protein") of the fish Aequorea Victoria and its many derivatives, or protein YFP ("Yellow Fluorescent Protein") as well as the protein luciferase.

Among the detectable molecules with catalytic activity, the preferred molecules are the following enzymes, according to the International Classification I.U.B.: (i) the oxidoreductases of class 1 and (ii) the hydrolases of class 3. The preferred oxidoreductases are (i) the dehydrogenases of class 1.1, most particularly 1.1.1, 1.1.3 and 1.1.99; (ii) the peroxidases of class 1.11; and (iii) the hydrolases of class 3.1, most particularly of class 3.1.3 and class 3.2, most particularly 3.2.1. The preferred dehydrogenases are malate dehydrogenase, glucose-6-phosphate dehydrogenase and lactate dehydrogenase. The preferred oxidase is glucose oxidase. The preferred peroxidase is horseradish peroxidase. The preferred hydrolases are the alkaline phosphatases, β-lucosidase and lyzozyme.

The detectable molecule may also be a radioactively marked molecule, for example by an isotope chosen from among [$^3$H], [$^{32}$P] and [$^{125}$I].

In the embodiment in which the detectable molecule comprises an indirect marker, one of the antibodies comprising the detection kit according to the invention may be covalently bound to a ligand such as biotin or streptavidine.

In this particular embodiment, the detectable molecule is chosen so that it fixes onto the ligand which is covalently bound to the antibody. The detectabl molecule may for example be itself bound respectively to biotin or to streptavidine.

According to another embodiment of a detection kit according to the invention, the means of revealing the formation of a complex between the protein ESM-1 present in the sample tested and one of the specific antibodies of protein ESM-1, may be an antibody, for example an antibody able to bind specifically to the Fc part of the anti-ESM-1 antibody or an antibody able to bind specifically to the isotype to which the anti-ESM-1 antibody belongs, for example an antibody specifically recognizing the mouse antibody of the isotype IgG1.

In a preferred embodiment of a detection kit according to the invention, it is the antibody specifically recognizing the C-terminal region of protein ESM-1 which is immobilized on a support.

Such a detection kit is advantageously that in which the antibody produced by the hybridoma MEP14 (CNCM N°I-1942) is immobilized on the support, is the antibody specifically binding to the N-terminal region of protein ESM-1 and the antibody produced by the hybridoma MEC15 (CNCM N°I-2672).

The detection tool may thus be a biotinylated monoclonal antibody, for example from a rat, specifically recognizing the mouse antibody of the isotype IgG1, the detection system being supplied by a streptavidine-peroxidase conjugate.

Immunodetection Method According to the Invention

A further object of the invention is a method for detecting protein ESM-1 in a sample characterized in that it comprises the following steps a) placing the sample to be tested in contact with a first antibody specifically binding to the N-terminal region of protein ESM-1 or with a first antibody binding to the C-terminal region of protein ESM-1.

b) placing the complex potentially formed between protein ESM-1 present in the sample and the first antibody in contact with a second antibody specifically binding to the region of protein ESM-1 chosen from among the N-terminal region and the C-terminal region not recognized by the first antibody; and c) detecting the complex formed between protein ESM-1 and the second antibody By "complex formed between protein ESM-1 and the second antibody" should be understood the complex formed between the complex formed between:

the complex formed between protein ESM-1 and the first antibody, and the second antibody.

According to a first embodiment of the immunodetection method above, the first or the second antibody may be immobilized on the surface of a support.

According to a second embodiment of the immunodetection method above, the antibody which is immobilized on a support is an antibody specifically binding to the C-terminal region of protein ESM-1 and the second antibody is an antibody specifically binding to the N-terminal region of this protein.

According to a third embodiment of the immunodetection method above, the antibody which is immobilized on a support is an antibody specifically binding to the N-terminal region of protein ESM-1 and the second antibody is an antibody specifically binding to the C-terminal region of this protein.

The antibodies specifically binding onto the N-terminal or C-terminal regions of ESM-1 are as defined above.

In a preferred embodiment of the detection method according to the invention, the antibody specifically binding to the N-terminal region of protein ESM-1 is the antibody MEC15 produced by the hybridoma deposited on 17 Oct. 2000 at the CNCM under the access number I-2572.

The second antibody may be the antibody MEP14 produced by the hybridoma deposited at the CNCM on 19 Nov. 1997 under the access number I-1942.

Step c) of the method described above may be performed using a biotinylated antibody able to fix to a second antibody, the detectable molecule being composed of a conjugate of the streptavidine-peroxidase type.

Application of the Detection Method According to the Invention

The applicant has shown that the method of immunodetection of protein ESM-1 according to the invention enables the serum concentration of protein ESM-1 in humans to be quantified with high sensitivity, in particular in patients suffering from sepsis, and enables a correlation to be established between the quantity of protein ESM-1 circulating and the severity of the sepsis in the patients.

According to the standard defined by the American College of Chest Physicians/Society of Critical Care Medicine Consensus Conference (1992, definitions for sepsis and multiple organ failure, and guidelines for the use of innovative therapies in sepsis; Crit Care Med., vol. 20: 864-874), sepsis may be divided into three categories of increasing severity: sepsis, severe sepsis and septic shock.

Thanks to the immunodetection method according to the invention, a correlation has been established between the severity of the sepsis and the concentration of protein ESM-1 circulating in the patients.

In addition, the high sensitivity of the immunodetection test according to the invention has shown that patients suffering from simple sepsis had a concentration of circulating protein ESM-1 which, although low, was significantly detectable and significantly higher ($p<0.001$) than the concentration of protein ESM-1 found in the serum of healthy volunteers.

Up until now, the development of sepsis in a patient was monitored by the quantification of three markers, respectively C-reactive protein, soluble ICAM-1 protein and procalcitonin.

It has been shown according to the invention that the development of the levels of C-reactive protein and of soluble ICAM-1 protein do not correlate with the development of the concentration of ESM-1.

In contrast, there is a good correlation between the development of the levels of procalcitonin and of protein ESM-1. However, the biological significance of procalcitonin in the case of sepsis is not known and this protein therefore does not represent a good biological marker for the development of sepsis.

On the other hand, protein ESM-1, due to its role in the regulation of inflammatory reactions, constitutes a new marker of the development of sepsis whose physiological significance is directly linked to the uncontrolled development of the inflammatory reaction, particularly the recruitment of leukocytes during the phenomena of extravasation and massive infiltration of these cells in different tissues, especially lung tissue, which are causal, or at the least concomitant, phenomena, with a deterioration of the endothelial vascular wall.

The applicant has thus shown that the immunodetection test of the invention enables low concentrations of circulating protein ESM-1 to be detected, of the order of 1 to 3 nanogram per milliliter, these low concentrations found in atopic patients may be dearly distinguished from the base concentrations of the order of nanogram/ml or even lower measured in healthy volunteers.

In addition, it has been shown that the quantity of serum ESM-1 found in patients suffering from sepsis represents a reliable diagnosis of mortality for these patients. Thus, for 68 patients tested, the patients having died 10 days after their hospitalization presented concentrations of circulating ESM-1 at day 0 and at day 1 significantly higher than the concentrations of ESM-1 found in the serum of patients having survived (10.6±0.8 nanograms per ml in deceased patients against 4.0±0.6 nanograms per ml in patients having survived [p>0.01]).

This close correlation between the level of circulating protein ESM-1 and the prognosis of mortality of the patients has not been found for the conventional markers of sepsis, in other words C-reactive protein, procalcitonin and soluble ICAM-1 protein.

However, the measurement of the concentration of circulating ESM-1 alone in a patient is not sufficient for performing a medical diagnosis permitting the doctor to take therapeutic measures suitable for the overall state of the patient.

A further object of the invention consists of the use of a detection kit for protein ESM-1 according to the invention to detect in vitro deteriorations of the endothelial vascular wall in man, and particularly in patients.

The invention also relates to the use of a detection kit for protein ESM-1 as defined above for monitoring in vitro a marker of the severity of a sepsis in a patient.

It has also been shown according to the invention that a concentration of circulating protein ESM-1 higher than normal is found in patients having undergone organ transplants and treated with an immunosuppressant compound. The increase in the concentration of circulating protein ESM-1 is indicative of a cytotoxic activity of the immunosuppressant compound against endothelial cells, particularly endothelial cells of the vascular wall.

Thus, the use of a detection kit for protein ESM-1 according to the invention makes it possible to monitor patients treated with immunosuppressant compounds and to determine the time when these immunosuppressants become cytotoxic.

The detection of levels of circulating ESM-1 higher than normal in these patients may represent an indication for the doctor to moderate the doses of immunosuppressant compounds administered, when this measurement is accompanied by other physiological parameters in the patient.

According to a further aspect, the invention concerns the use of an immunodetection kit according to the invention for the quantification of protein ESM-1 in vitro in a patient treated with an immunosuppressant compound, in particular in a patient having undergone an organ transplant.

The applicant has also shown a significant increase of the level of circulating protein ESM-1 in patients suffering from cancer, in particular broncho-pulmonary cancer.

According to yet another aspect, the invention concerns the use of an immunodetection kit such as defined above for the quantification in vitro of protein ESM-1 in a patient suffering from cancer.

In general, a level of circulating protein ESM-1 higher than 1 nanogram per ml is significant of a deterioration of the endothelial cells of the vascular wall and may thus represent a parameter to be taken into account during the establishment of a clinical diagnosis of a patient by a doctor, it being understood that this parameter alone, taken in isolation, cannot in itself establish a therapeutic or clinical diagnosis for a patient.

The present invention is in addition illustrated, without in any way being limited, by the following figures and examples.

FIGURES

FIG. 1 illustrates a comparison of the sensitivity of detection of the immunodetection test for protein ESM-1 according to the invention (open circles) with the detection test described by BECHARD et al. (2000) represented by solid circles. The ordinate represents the concentration of protein ESM-1 in the sample to be tested, expressed in nanograms per ml. The optical density is represented on the abscissa.

FIG. 2 illustrates the immunodetection profiles performed according to the immunoenzymatic technique of the "sandwich" type. In all cases, the monoclonal antibody produced by the hybridoma MEP14 was adsorbed on a micro-titration plate. The optical density is represented on the abscissa. The ordinate represents the concentration in protein ESM-1 produced by the cells of the line HEK293, expressed in nanograms per ml. The second antibody used in the immunodetection test was an antibody directed specifically against the N-terminal region of protein ESM-1. It was antibody MEC2 (FIG. 2A), MEC15 (FIG. 2B) and MEC36 (FIG. 2C).

FIG. 3 illustrates a comparison of the concentration of protein ESM-1 found in the plasma or the serum of healthy volunteers or of patients. The ordinate represents the serum concentration of protein ESM-1, expressed in nanograms per ml. the abscissa represents the plasma concentration of protein ESM-1, expressed in nanograms per ml.

FIG. 4 illustrates the quantity of circulating protein ESM-1 found in the serum of healthy volunteers or of patients suffering from sepsis of increasing clinical severity. The concentration of serum protein ESM-1, expressed in nanograms per ml, is shown on the ordinate. The abscissa shows the different populations of individuals tested, respectively healthy subjects (CTRL), patients suffering from sepsis, severe sepsis or septic shock, according to the clinical definition published in Crit. Care Med., 1992, vol. 20:864-874.

FIG. 5 illustrates the quantification of three sepsis markers in populations of healthy patients, or of patients suffering from sepsis, severe sepsis or septic shock.

FIG. 5A illustrates the quantification of soluble ICAM-1 protein in the serum, expressed in nanograms per ml.

FIG. 5B illustrates the quantification of C-reactive protein, expressed in milligrams per ml.

FIG. 5C illustrates the quantification of serum procalcitonin, expressed in nanograms per ml.

FIG. 6 illustrates a comparison between the levels of circulating protein ESM-1, and of each of the three conventional sepsis markers, respectively soluble ICAM-1 protein, C-reactive protein and Ia procalcitonin at day 0 of hospitalization of the patients, respectively in patients having survived and patients having died.

FIG. 6A illustrates the serum level of protein ESM-1, expressed in nanograms per ml.

FIG. 6B illustrates the serum level of soluble ICAM-1 protein, expressed in nanograms per ml.

FIG. 6C illustrates the serum level of C-reactive protein, expressed in nanograms per ml.

FIG. 6D illustrates the level of procalcitonin, expressed in nanograms per ml.

FIG. 7 illustrates the prognostic value of the quantity of protein ESM-1 or of soluble ICAM-1 protein in patients at day 0 and at day 1 after hospitalization, compared to their mortality.

FIG. 7A illustrates the level of protein ESM-1, expressed in nanograms per ml, found respectively in patients having survived (solid circle) and patients having died (open circle), at day 0 and day 1 after hospitalization.

FIG. 7B illustrates the level of serum soluble ICAM-1 protein in the same patients.

FIG. 8 illustrates the mortality prognostic value of the level ESM-1 and soluble ICAM-1 protein measured at day 0 and at day 1 after hospitalization.

FIG. 8A illustrates the level of serum protein, expressed in nanograms per ml, in patients having survived (solid circle) and patients having died (open circle).

FIG. 8B illustrates the level of serum soluble ICAM-1 protein, expressed in nanograms per ml, in patients having survived (solid circle) and patients having died (open circle)).

EXAMPLES

Example 1

Figure 1:
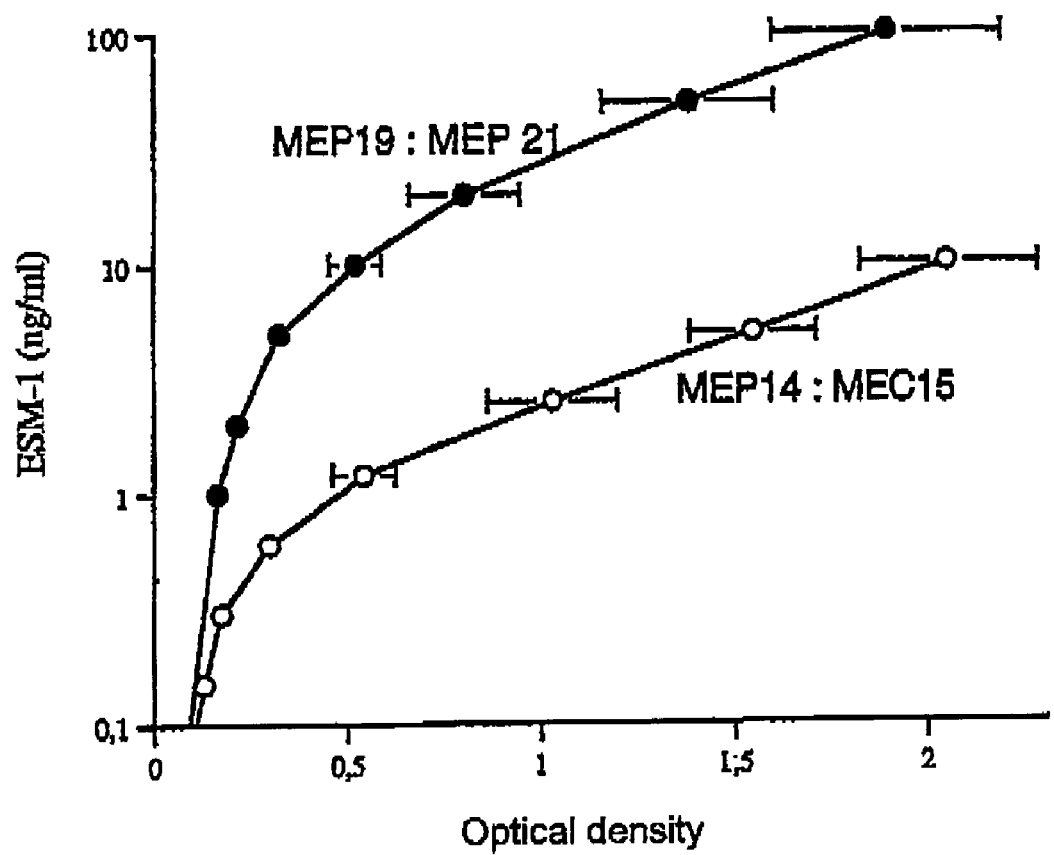

Preparation of Monoclonal Antibodies Specifically Binding to the N-terminal Region of Protein ESM-1 Produced by Eukaryotic Cells In order to obtain anti-ESM-1 monoclonal antibodies directed against the N-terminal region of protein ESM-1 rich in cysteine residues, the native form of protein ESM-1 produced by a CHO cell line transfected by an expression vector containing a DNA insert coding for protein ESM-1 was purified.

The cDNA sequence coding for protein ESM-1 is referenced as sequence SEQ ID N°2 in the list of sequences.

The cDNA of ESM-1 was inserted into the eukaryotic expression vector pcDNA3 (In vitrogen) then transfected in CHO cells with lipofectamine (Gibco) according to the recommendations of the manufacturer. 48 h after the transfection the cells were subcultured in the presence of a selection agent (G418, Gibco) at a dose of 1000 micrograms/ml). After two weeks of selection the CHO cells resistant to G418 were cloned by limiting dilution. The clones expressing ESM-1 were then selected and named CHO-ESM (deposited at the CNCM).

For the production, the CHO-ESM cells were cultured in suspension in a medium without foetal calf serum (medium CHO SFM II, Gibco). The supernatant was adjusted to pH 8 and passed over a column of DEAE-sepharose (Pharmacia). The column was washed with a buffer 50 mM Tris, pH 8, 0.2 M NaCl. The pmolecule ESM-1 was eluted in a buffer 50 mM Tris, pH 8, 1 M NaCl. The eluate was then diluted 1:4 in a buffer 50 mM Tris, pH 8 and incubated in the presence of anti-ESM-1 monoclonal antibody (MEC4) immobilized on agarose (Biorad). After one night of incubation at 4° C. with agitation, the agarose beads were washed with the buffer 50 mM Tris, pH 8, 0.2 M NaCl. ESM-1 was eluted with 3 M $MgCl_2$, the eluate was concentrated and dialysed in the buffer 50 mM Tris, pH 8, 0.5 M NaCl and stored at −70° C.

Balb/C mice were immunized by injection of 10 µg of purified recombinant protein ESM-1 per mouse, according to a standard immunization protocol in the presence of Freund's adjuvant.

Hybridoma cells secreting anti-ESM-1 monoclonal antibodies were obtained by fusion, screening and sub-cloning according to the technique described by BECHARD et al. (2000).

Five hybridoma cell clones were obtained and were generically designated MEC ("Mouse Monoclonal Antibody to ESM-1 produced by CHO Cells").

Four of the hybridomas selected were of isotype IgG1,k respectively the hybridomas designated MEC4, MEC5, MEC15 and MEC36.

One of the hybridomas was of isotype IgM,k, the hybridoma MEC11.

The hybridoma cell clones were cultured in a culture medium in the absence of serum and the anti-ESM-1 antibodies were purified by chromatography on a column of protein G-Sepharose marketed by Pharmacia (UPPSALA, Sweden).

Example 2

Selection of the Monoclonal Antibodies Specifically Directed Against the N-terminal Part of Protein ESM-1 Produced by Cells of the CHO Line The MEC antibodies of class IgG1,K were selected by the persistence of a strong binding between the antibodies of the MEC series and ESM/Fc in the presence of MEP antibody of different isotype and at a final concentration of 1 µg/ml. The tests were performed by ELISA according to the examples above for the selection of the MEP and MEC antibodies (particularly by the immuno-detection by competition experiments described by LASSALLE et al. (1996).

Example 3

Immuno-detection Test for Protein ESM-1 According to the Invention

The immuno-detection test consisted of an immuno-enzymatic test of the "sandwich" type whose overall characteristics were identical to that described by BECHARD et al. (2000).

The anti-ESM-1 monoclonal antibody produced by the hybridoma line MEP14 (CNCM N°I-1942) was diluted to a concentration of 5 µg/ml in a buffer carbonate 0.1 M, pH 9.5, and adsorbed overnight at +4° C. on a 96-well plate (plate E.I.A./R.I.A., Costar, Cambridge, Mass., USA).

The plate was saturated for one hour at laboratory temperature with a volume of 200 µl/well of PBS buffer containing 0.1% of bovine serum albumin and 5 mM of EDTA, then washed twice with an ELISA buffer (the PBS buffer above supplemented with 0.1% of Tween 20).

A calibration was performed with purified protein ESM-1 according to the technique described by BECHARD et al. (2000).

Blood samples were serially diluted (1:2 to 1:128), in an ELISA buffer and incubated on an ELISA plate for one hour at laboratory temperature.

The wells were washed three times with an ELISA buffer then incubated for 1 hour at laboratory temperature with a second monoclonal antibody directed against ESM-1, the antibody MEC15 (CNCM N°I-2572) at a concentration of 0.1 µg/ml in 100 µl of buffer per well.

After three washings, a biotinylated rat monoclonal antibody directed against mouse IgG1 (marketed by PHARMINGEN) diluted in an ELISA buffer was added and left to incubate for one hour.

After three washings in ELISA buffer, the wells were incubated with a streptavidine-peroxidase conjugate at a dilution 1:10.000 v/v (marketed by ZYMED).

After 30 minutes of incubation with the streptavidine-peroxidase conjugate, three washings of each well were performed in an ELISA buffer, then two washings in a PBS buffer.

The streptavidine-peroxidase conjugate was revealed with the substrate TMB marketed by SIGMA (Saint-Louis, Mo., USA) in the presence of 5 µl of $H_2O_2$ for 30'.

The revelation reaction was stopped by addition of a volume of 100 µl of $H_2SO_4$ 2N.

The plate was read using a spectrophotometer (anthos labtec LP40. France) at a wavelength of 405 nanometers.

The plasma or serum concentration of protein ESM-1 was calculated from the optical density measurements and expressed in nanograms per ml.

Example 4

Comparative Results of the Determination of ESM-1 with the Immuno-detection Test According to the Invention and an Immuno-detection Test of the State of the Art Comparative determinations of known concentrations of recombinant protein ESM-1 produced by the transfected CHO cell line, and then purified as described in example 1, were performed.

The first determination was performed in accordance with the teaching of example 3. Briefly, the antibody MEP14 was immobilized on a 96-well plate of the ELISA type, then placed in contact with a series of PBS buffer solutions containing a known concentration of protein ESM-1. After washing, the complex formed between the immobilized antibody MEP14 and protein ESM-1 was incubated with a buffer solution containing the antibody MEC15 of the invention.

After a further series of washings, the antigen/antibody complex formed was incubated successively with a biotinylated rat anti-IgG1 mouse, then with a streptavidine-peroxidase conjugate before revelation with hydrogen peroxide.

The second test was performed under the same conditions, but using the antibody MEP19 immobilized on a 96-well plate of the ELISA type and the antibody MEP21 as the second antibody in this immunoenzymatic technique of the "sandwich" type.

The results are given in FIG. 1.

With the combination of antibodies according to the invention, a significant difference of the optical density value was obtained with a concentration of protein ESM-1 of the order of 0.15 to 0.2 nanograms per milliliter.

In contrast, with the combination of the antibodies MEP19 and MEP21, a significant increase in the optical density value was only obtained for a concentration of ESM-1 equal to 1 or 2 nanograms per ml.

The results given in FIG. 1 clearly show the high sensitivity of the immunodetection test for protein ESM-1 according to the invention, compared to an immunodetection test of the state of the art, since a sensitivity difference of between 5 and 10 fold can be observed between these two tests, in favour of the immunodetection test of the invention.

Example 5

Comparative Results of Immunodetection Tests Using Different Antibodies of the Invention Directed Against the N-terminal Region of Protein ESM-1 Produced by Transfected Cells of the Line HEK293

Immunodetection tests of the "sandwich" type were performed in accordance with the protocol described in example 3.

In all cases, the antibody MEP14 was immobilized in the wells of a 96-well plate of the ELISA type. After incubation of the plate thus prepared with solutions of known concentrations of recombinant ESM-1 produced by transfected cells of the line HEK293 and washing, the antigen/antibody complex formed was incubated in the presence of a second antibody, respectively the antibody MEC2, the antibody MEC15 and the antibody MEC36.

Figure 2:
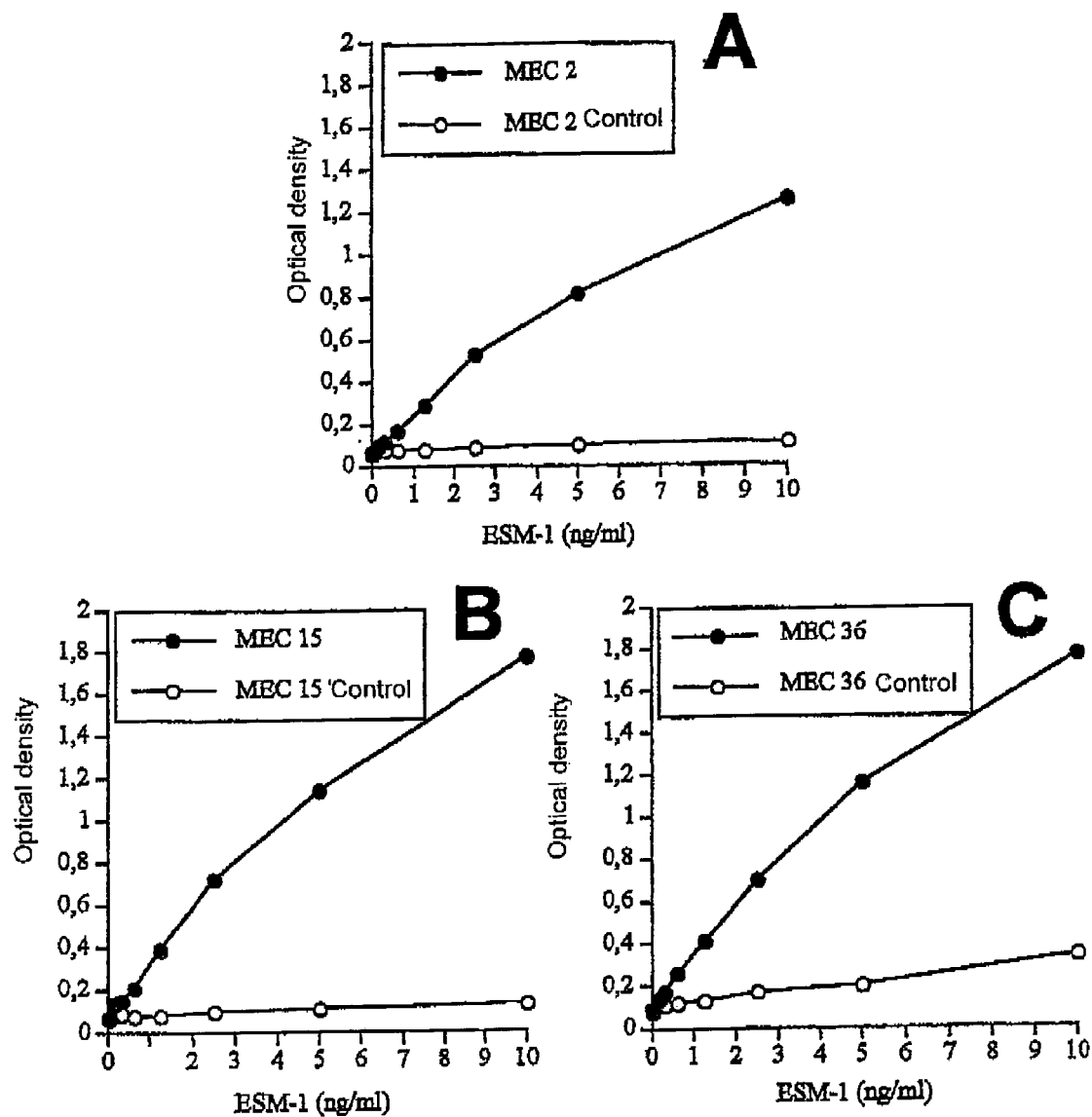

The results are given in FIG. 2.

The results show that the use of the monoclonal antibodies directed against the N-terminal region of recombinant protein ESM-1 produced by eukaryotic cells in an immunoenzymatic test of the "sandwich" type leads to a determination of protein ESM-1 of very high sensitivity, and thus the sensitivity is reproducible from one antibody to another.

For the group of antibodies MEC15, MEC2 and MEC36 tested, concentrations of the order of 0.15 to 0.2 nanograms per ml of ESM-1 could be detected.

Example 6

Application of the Immuno-detection Test According to the Invention to Quantifier Circulating Protein ESM-1 in Patients Suffering from Sepsis of Different Levels of Severity A. Materials and Methods.

A.1 Immuno-detection Test

The immunodetection test was performed in accordance with the protocol described in example 3 above.

A.2. Test of Other Blood Markers

The quantitative test of serum soluble ICAM-1 protein was performed with a commercial ELISA test (Diaclone Research, Besançon, France). The plate was read using a spectrophotometer (Anthos Labtec LP40. France) at a wavelength of 450 nanometers. The concentration of serum soluble ICAM-1 was calculated from the measurements of optical density and expressed in nanograms per ml, The normal value of the concentration of soluble ICAM-1 protein was 571±168 nanograms per ml (219-1042; n=77).

The test of quantification of the protein procalcitonin was performed with an immunological test of the ILMA type (Lumitest, B.R.A.M.S.-Diagnostica GmbH, Germany).

The normal value of procalcitonin is lower than 0.5 nanograms per ml. The values measured for patients suffering from Systemic Inflammatory Response Syndrome (SIRS) were generally between 0.5 and 2 nanograms per ml.

The quantity of C-reactive protein was measured by immuno-nephelometry. The normal value was lower than 10 mg/l (Morley et al., 1982, Ann. N.Y. Acad. Sci., vol. 389:406-418).

A.3 Subjects

The study was performed with four groups of subjects, one group of non-atopic healthy subjects (sex ratio 1) and three groups of patients suffering from systemic and/or pulmonary septic inflammatory problems (sex ratio 1.6, age: 56±2 years).

All the non-atopic healthy subjects showed a negative response to the immediate hypersensitivity cutaneous reaction test (prick test), and showed no clinical history of allergies.

None of the 68 patients was treated with corticosteroids or had undergone hemodialysis when blood samples were taken.

The experimental protocol was approved by the Local Ethics Committee of the Swiss University Hospitals.

A.4 Definitions.

The following terms have been used in this study.

Infection is a microbial phenomenon characterized by an inflammatory response in the presence of micro-organisms or on the invasion of normally sterile tissue of the host by these microorganisms.

Systemic Inflammatory Response Syndrome (SIRS) with no sign of infection, is characterized by the presence of at least two of the four following clinical criteria:

a) fever or hypothermia (temperature above 100.4° F. [<38° C.] or >96.8° F.[>36° C.]);

b) tachycardia (>90 beats per minute);

c) tachypnea (>20 breaths per minute or $PaCO_2$<4.3 kPa [32 mm Hg]); and d) an abnormal white blood cell count >12.000 cells/$mm^3$; <4000 cells/$mm^3$, or the presence of more than 10% of immature forms respectively.

Sepsis is defined as SIRS accompanied by an infection.

Severe sepsis is defined as a sepsis associated with a malfunction, a hypoperfusion or a hypotension of an organ, Abnormalities in hypoperfusion and perfusion may include, but are not limited to, oliguria (volume excreted <30 ml/hr), lactic acidosis (level of serum lactate greater than 2 mmol/L) or an acute deterioration of the mental state without sedation (reduction of at least 3 points with respect to the base value according to the coma score of the Glasgow type).

Septic shock is defined as the presence of a sepsis accompanied by a lasting reduction in the systolic blood pressure (<90 mmHg, or a reduction of 40 mm Hg compared to the base value of the systolic blood pressure), associated with the presence of perfusion abnormalities (see above), despite appropriate resuscitation and the need for vasoactive amines to maintain adequate blood pressure (Crit. Care Med. 1992, vol. 20:864-874).

A.5 Description of the Study

For each patient, the following biological and clinical parameters were obtained: age, sex, principal and secondary diagnosis as defined in Crit. Care ed., 1992, vol. 20: 864-874, antecedents, treatment, vital state 10 days before blood sampling, serum and plasma concentrations of protein ESM-1.

For most of the patients, other blood biological parameters were also measured such as circulating soluble ICAM-1 (sICAM-1), procalcitonin (proCT), and C-reactive protein (CRP).

Blood samples were taken from each of the patients (or healthy volunteers) in dry tubes and in tubes treated with EDTA, the centrifuged for 30 mn at a speed of 3500 r.p.m. in a centrifuge of type jouan C3I (France).

The serum and plasma samples were stored for a short time at −20° C. before the tests were performed.

The survival period of 10 days hospitalization was chosen by postulating that the infection had directly contributed to death in these patients or that the contribution of the initial inflammatory problem compared to other causes of mortality could not be excluded.

A.7 Statistical Analysis

The data are expressed as the mean plus or minus the standard deviation.

The comparisons of mean levels of ESM-1, sICAM-1, procalcitonin and CRP between the different groups were performed using the "One way Analysis" test Anova (Bonferroni-Dunn), the Kruskal-Wallis test and the Mann-Whitney test.

The correlation between the values of the markers was performed using the Spearman Rank test.

The correlation between the level of circulating marker and the severity of the patient's situation was performed using the "One Way" test ANOVA (Bonferroni-Dunn), the Mann-Whitney test and the Wilcoxon test.

In general, a value of $p<0.05$ was considered as statistically significant.

The graphs were produced in the form of graphs in vertical bars represented by their median and the first and third quartiles.

B. Results

B.1 Correlation Between the Plasma and Serum Levels of ESM-1.

Figure 3:
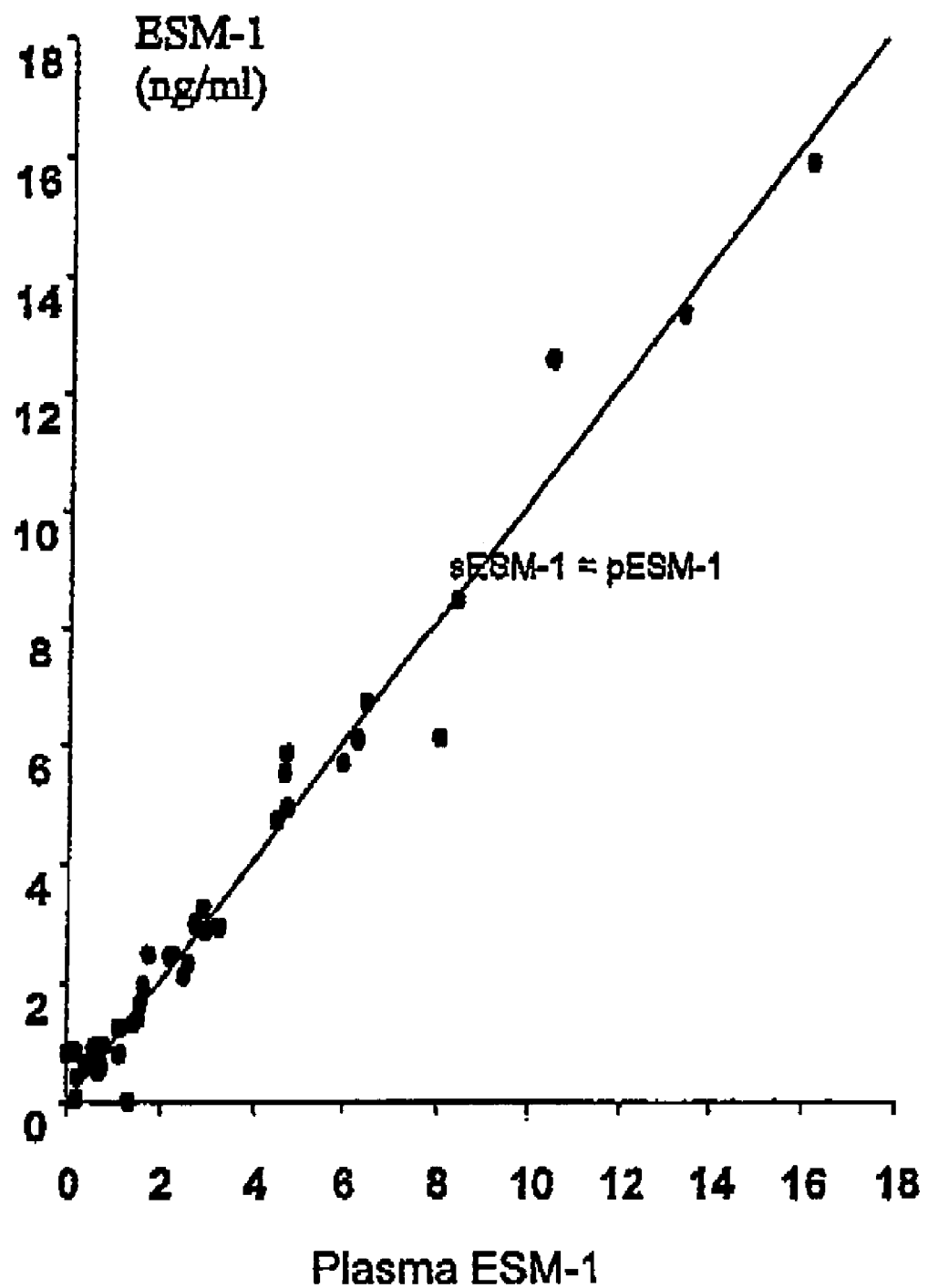

In a first test, it was determined if the conditions of taking the blood samples could affect the value of the ESM-1 level. The comparison of the values of the plasma and serum levels of ESM-1 in 41 healthy subjects had shown a strong correlation ($r=0.85$; $p<0.0001$). In FIG. 3, it can be observed that, as for the control group, no significant difference can be detected for a given patient between the plasma and serum levels of ESM-1, for the first 36 patients of the study.

These results suggest for a start that the coagulation of the blood does not alter the ESM-1 level. These results also suggest that protein ESM-1 may be quantified either from blood or plasma samples.

Therefore, only the serum level of ESM-1 was used for the rest of the study.

B.2 Control Group

A mean value of the serum level of ESM-1 was 0.7±0.4 nanograms per ml in healthy subjects, as shown in table 1, while the serum level of ESM-1 was 1.0+/−0.1 nanograms per ml in the group of atopic subjects.

Although the difference was small, it was statistically significant ($p<0.05$).

In consequence, the control group referred to in the study is the group of healthy non-atopic subjects representative of the general population, and the mean value of the ESM-1 level in this group of healthy non-atopic subjects was determined to be the standard normal value.

B.3. Groups of Patients

Figure 4:
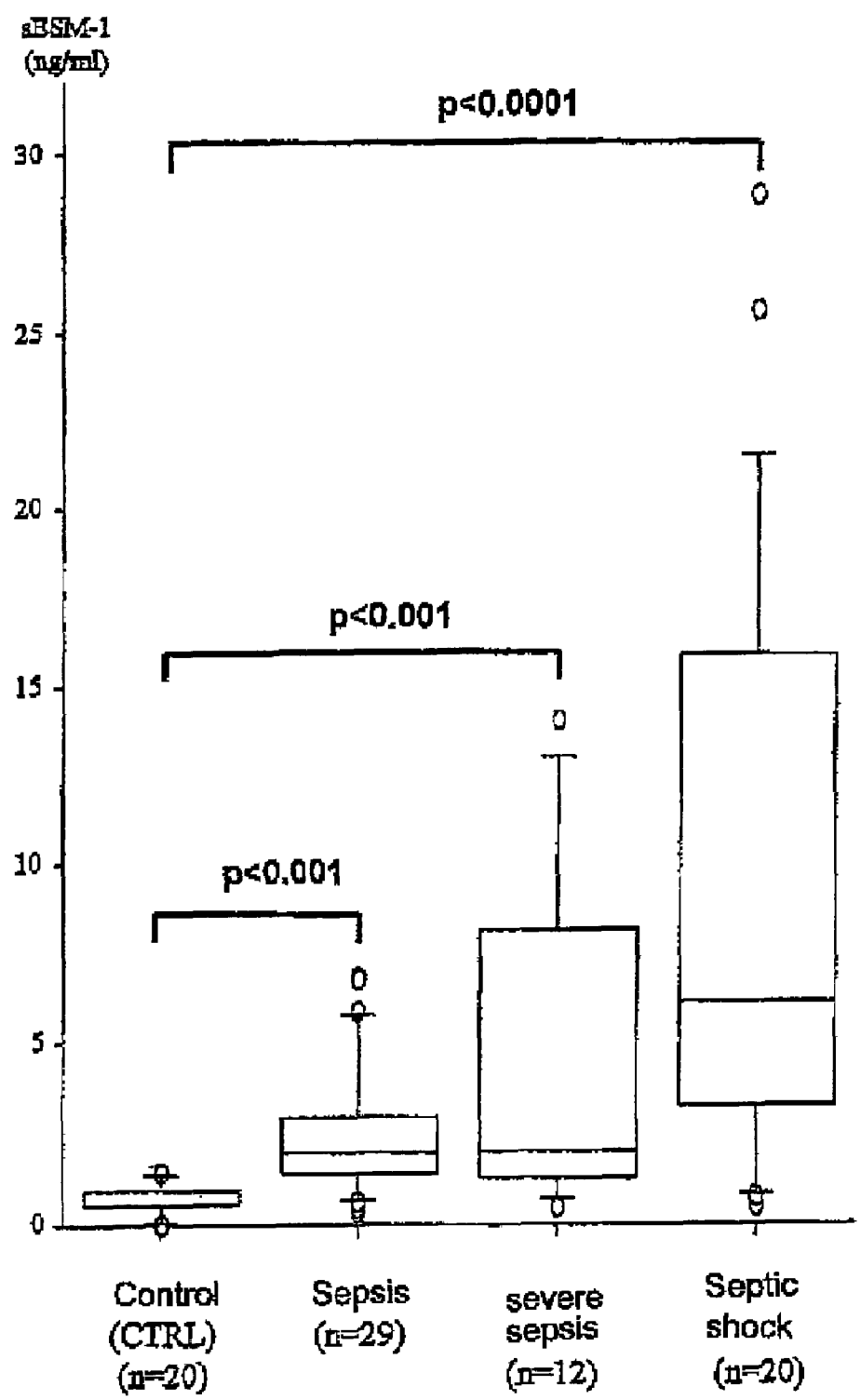

The results of the circulating markers in the groups of patients are summarized in table 1 and illustrated in FIGS. 4 and 5.

In the serum of patients admitted for severe sepsis, the levels sESM1, sICAM-1, CRP and proCT were strongly increased for each group of patients, compared to the control group (table 1).

These increased levels were statistically significant ($p<0.01$ or less) for all the markers and for all the groups of patients, with the exception of procalcitonin in the group of patients suffering from sepsis (table 1, FIGS. 4 and 5).

The severity of the disorder was defined according to three levels designated respectively sepsis, severe sepsis and septic shock. In each of these groups, the ESM-1 levels increased in a way statistically correlated with the severity of the disorder (p<0.01, n=61) (see table 2).

Similar increases were found for the serum procalcitonin and CRP levels (respectively p=0.0001, n=34 and p<0.01, n=43).

However, the level of sICAM-1 increased to about 5 times the normal value, but showed a similar level in each of the groups of patients.

The CRP (Anova and Mann-Whitney) and ProCT levels (Mann-Whitney) enabled the groups of patients suffering from sepsis to be distinguished from the patients suffering from severe sepsis, which was not the case for the ESM-1 levels.

The ESM-1 (Anova and Mann-Whitney) and ProCT levels (Mann-Whitney) enabled the groups of patients suffering from severe sepsis to be distinguished from the patients suffering from septic shock, which was not the case for the CRP levels (see table 2).

In view of these results, the CRP seems to be the most sensitive marker for the least severe disorder and the ESM-1 level seems to be a better marker then the ProCT marker for the more severe sepsis.

A search for correlation between the serum levels of ESM-1, sICAM-1, CRP or ProCT established a significant correlation between the CRP and procalcitonin levels (p<0.01, table 3).

However, no correlation was found between the other markers (see table 3).

In addition, no correlation was observed between the levels of ESM-1 and of plasma creatinine in the group of patients suffering from septic shock (results not shown).

In order to determine if the serum levels of ESM-1 could predict a vital prognosis, a first approach was to compare the mean levels of serum ESM-1 between the patients having died and the patients having survived.

When all the patients were taken into account from admission for resuscitation and according to a fatal outcome or not, the results showed that the level of serum ESM-1 at the day of hospitalization (day 0) was significantly greater in the group of patients having died at day 10 (day 10; p<0.01; FIG. 6A and FIG. 7A). It may be emphasized that such differences were not shown with the other markers sICAM-1, CRP or ProCT (FIGS. 6B-9).

In a second approach, the level is of sESM-1 and s-ICAM1 were measured both on the day of hospitalization (day 0) and 24 hours after (day 1). The level of ESM-1 at day 0 was significantly higher in patients having died than in patents having survived (FIG. 7A). This difference persisted at day 1 (n=20. p<0.05) (FIG. 7A).

Such a difference could not be observed with any of the other markers sICAM-1 (FIG. 7B) nor with CRP, procalcitonin or sICAM-1.

In the group of patients suffering from septic shock only, the serum levels of ESM-1 at day 0 and at day 1 (n=11) were significantly higher in patients having died than in patients having survived (FIGS. 8A-B).

In each group separately, no statistically significant correlation was found between the levels of sICAM-1 at day 0. of sICAM-1 at day 1 (FIG. 8B), of CRP at day O, or of ProCT at day 0 and the survival at day 10 of each patient.

The results presented in this example show that the mean value of the concentration of circulating protein ESM-1 is greatly increased compared to healthy subjects. This increase of the mean concentration of circulating ESM-1 is correlated with the level of clinical severity of the disorder. The highest levels of circulating ESM-1 at the early stages of the disorder were associated with a lower probability of survival of the patient after 10 days.

In agreement with earlier studies, the circulating markers, such as C reactive protein or CRP (Morley et al.), procalcitonin or ProCT (ASSICOT M et al.); (MULLER B et al.), (WANNER G A et al.), and soluble ICAM-1 protein or sICAM-1 (KAVAL S et al.), (SESSLER C N et al. (1995) SESSLER C N et al. (1993) were also significantly increased in the patients of the study. The CRP and ProCT markers were correlated with the clinical severity of the patients.

However, the determination of the levels of the three markers CRP, ProCT and sICAM-1 did not allow prediction of vital prognosis, in contrast to the determination of the level of circulating protein ESM-1. In addition, the predictive value of the serum level of ESM-1 was predominantly linked to the initial value of serum ESM-1 at day 0 of hospitalization.

In this study, the increase of the level of serum ESM-1 did not correlate with renal malfunction, as measured by the increase of plasma creatinine level. This result suggests that the increased levels of protein ESM-1 in the serum in patents suffering from septic shock arise from deteriorated pulmonary tissue or from cells of the vascular walls in a stressed state.

In conclusion, the results of the study presented in this example show that ESM-1 represents a new marker of malfunction of the endothelial cells in patients suffering from sepsis.

In combination with values of other parameters of circulating markers such as the soluble adhesion molecules, the cytokines, procalcitonin or other markers of specific malfunction of certain cells, the level of protein ESM-1 supplies useful information on the clinical severity and outcome for patients suffering from sepsis.

TABLE 1

Values of the concentration of circulating protein ESM-1 in healthy volunteers and in different groups of patients suffering from sepsis

| | | Blood markers | | | |
|---|---|---|---|---|---|
| Group | n | sESM-1 (ng/ml) | sICAM-14 (ng/ml) | CRP (mg/l) | Procalcitonin (ng/ml) |
| Normal value (healthy non atopic) | 20 | 0.7 ± 0.1. | 571 ± 168 | <10 | <0.5 |
| All patients | 61 | 5.4 ± 0.8*** | 2510 ± 261*** | 194 ± 21*** | 39.8 ± 12.4*** |
| Sepsis (pulmonary) | 29 | 2.5 ± 0.3*** | 2336 ± 406*** | 126 ± 15*** | 2.0 ± 1.4 |

TABLE 1-continued

Values of the concentration of circulating protein ESM-1 in healthy volunteers and in different groups of patients suffering from sepsis

| | | Blood markers | | | |
|---|---|---|---|---|---|
| Group | n | sESM-1 (ng/ml) | sICAM-14 (ng/ml) | CRP (mg/l) | Procalcitonin (ng/ml) |
| Severe sepsis | 12 | 4.5 ± 1.4*** | 2696 ± 721* | 292 ± 73** | 23.8 ± 9.2*** |
| Septic shock | 20 | 10.0 ± 1.8*** | 2661 ± 373*** | 245 ± 29*** | 90.8 ± 29.5*** |

The values of the blood markers are expressed as the mean value±standard deviation. Significant difference between each group of patients and the normal value (group of healthy non-atopic subjects): *$p<0.01$; $p<0.0001$; *$p<0.0001$.

TABLE 2

Potential distinction of the severity of the state of the patient as a function of the level of the circulating markers

| | sESM-1 | sICAM-1 | CRP | ProCT |
|---|---|---|---|---|
| Markers showing a significant difference (ANOVA) | | | | |
| ECS and S/S | p < 0.01 | NS | NS | NS |
| ECS and S | p < 0.0001 | NS | p < 0.05 | p < 0.01 |
| S/S and S | NS | NS | p < 0.01 | NS |
| Kruskal-Wallis | p < 0.01 | NS | p < 0.01 | p = 0.0001 |
| Markers showing a significant difference (Mann-Whitney) | | | | |
| ECS et-S/S | p < 0.05 | NS | NS | p < 0.05 |
| ECS and S | p < 0.001 | NS | p < 0.01 | p = 0.0001 |
| S/S and S | NS | NS | p < 0.05 | p < 0.01 |

NS = non significant.

TABLE 3

Correlation between the different values of the blood markers

| Marker | sESM-1 | pESM-1 | Age | 1ICAM-1 | CRP | ProCT | Plasma creatinine |
|---|---|---|---|---|---|---|---|
| sESM-1 | — | p < 0.0001 | NS | NS | NS | NS | NS |
| sICAM-1 | NS | — | — | — | NS | NS | — |
| CRP | NS | — | — | NS | — | p < 0.01 | — |
| ProCT | NS | — | — | NS | p < 0.01 | — | — |

NS = non significant.

REFERENCES

AMERICAN COLLEGE OF CHEST PHYSICIANS/SOCIETY OF CRITICAL CARE MEDICINE CONSENSUS CONFERENCE (1992).

ASSICOT M et al., 1993, Lancet, vol. 341: 515-518

BECHARD et al. (2000) J. Vasc. Res., vol. 37 (5): 417-425.

ICHINOSE N et al. (1991, In: Fluorometric analysis in Biomedical Chemistry, vol. 10, page 110. Chemical Analysis, Winefordner J D et al. editor, John Wiley and Sons, New York)

KAYAL S et al., 1998, Am. J. Respir. Crit Care Med, vol. 157:774-776;

KOHLER and MIELSTEIN (1975, Nature, vol. 256:495)

KOZBOR et al. (1983, hybridoma, vol. 2 (1): 7-16).

LASSALLE P et al. (1996) The Journal of Biological Chemistry, vol. 271(34): 20.458-20.464).

LEGER et al., (1997, Hum. Antibodies, Vol. 8 (1): 3-16).

MARTINEAU et al. (1998, J. Mol. Biol., vol. 280 (1): 117-127).

MORLEY et al., Ann. N.Y. Acad. Sci, 1982, vol. 389:406-418),

MULLER B et al (2000), Crit. Care Med., vol. 28:977-983;

RIDDER et al; (1995, Biotechnology NY), vol. 13 (3): 255-260).

REINMANN et al. (1997, AIDS Res. Hum. Retroviruses, vol. 13 (11):933-943)

SESSLER C. N. et al., Am. J. Respir. Crit Care Med., 1995, vol. 151:1420-1427;

SESSLER C. N., 1993, Chest, vol. 104 (2): 11S)

WANNER et al., 2000. Crit. Care Med., vol 28 (4): 950-957

The invention claimed is:

1. Hybridoma line MEC15 deposited at CNCM on 17 Oct. 2000 under accession number I-2572.

2. A monoclonal antibody produced by hybridoma line MEC15 deposited on 17 Oct. 2000 at the CNCM under accession number I-2572.

3. A kit for detecting protein ESM-1 in a sample, comprising:
   a) a first antibody comprising a monoclonal antibody produced by hybridoma line MEC 15 deposited at Collection de Cultures de Micro-organismes (CNCM) of Institut Pasteur on 17 Oct. 2000 under accession number I-2572; and
   b) a second antibody specifically binding to a C-terminal region of protein ESM-1 contained between amino acid in position 79 and amino acid in position 184 of SEQ ID NO: 1.

4. The kit for detection according to claim 3, wherein the second antibody is chosen from among antibodies able to recognize an antigenic determinant selected from the group consisting of:
   a) the antigenic determinant AgD1 running from proline in position 79 to cysteine in position 99 of SEQ ID NO: 1,
   b) the antigenic determinant AgD2 running from serine in position 119 to valine in position 139 of SEQ ID NO: 1; and
   c) the antigenic determinant AgD3 running from glycine in position 159 to arginine in position 184 of SEQ ID NO: 1.

5. The kit for detection according to claim 4, wherein the second antibody comprises a monoclonal antibody selected from the group consisting of:
   a) the monoclonal antibody MEP 21 produced by a hybridoma line deposited at CNCM on 19 Nov. 1997 under accession number I-1944;
   b) the monoclonal antibody MEP08 produced by a hybridoma line deposited on 19 Nov. 1997 at CNCM under accession number I-1941;
   c) the monoclonal antibody MEP14 produced by a hybridoma line deposited on 19 Nov. 1997 at CNCM under accession number I-1942; and
   d) the monoclonal antibody MEP19 produced by a hybridoma line deposited on 19 Nov. 1997 at CNCM under accession number I-1943.

6. The kit for detection according to claim 3, wherein at least one of the two antibodies is covalently linked to a molecule enabling its direct or indirect detection.

7. The kit for detection according to claim 3, wherein the first or the second antibody is immobilized on a support.

8. The kit for detection according to claim 7, wherein the antibody immobilized on a support is the antibody specifically recognizing the C-terminal region of protein ESM-1.

9. A method for detecting protein ESM-1 in a sample comprising the following steps:
- a) placing a sample to be tested in contact with a first antibody, wherein the first antibody is selected from:
  - (i) an antibody specifically binding to a N-terminal region of protein ESM-1 contained between amino acid in position 20 and amino acid in position 78 of SEQ ID NO: 1 comprising a monoclonal antibody produced by hybridoma line MEC 15 deposited at Collection de Cultures de Micro-organismes (CNCM) of Institut Pasteur on 17 Oct. 2000 under accession number 1-2572, or
  - (ii) an antibody specifically binding to a C-terminal region of protein ESM-1 contained between amino acid in position 79 and amino acid in position 184 of SEQ ID NO: 1;
- b) placing a complex potentially formed between the protein ESM-1 present in the sample and the first antibody in contact with a second antibody, wherein the second antibody is selected from (i) or (ii) and binds to the region of ESM-1 not recognized by the first antibody; and
- c) detecting the complex formed between protein ESM-1 and the second antibody.

10. The method of detection according to claim 9, wherein the first antibody is immobilized on a support.

11. The method of detection according to claim 9, wherein the first antibody is an antibody specifically binding to the C-terminal region of protein ESM-1 and the second antibody is a monoclonal antibody produced by hybridoma line MEC 15 deposited at Collection de Cultures de Micro-organismes (CNCM) of Institut Pasteur on 17 Oct. 2000 under accession number I-2572.

12. The method of detection according to claim 9, wherein step c) comprises detecting the complex with a biotinylated antibody able to fix to the second antibody.

13. A method of quantifying protein ESM-1 in vitro in a sample comprising measuring protein ESM-1 in the sample with the kit of claim 3.

14. A method for detecting elevated levels of protein ESM-1 in a plasma or serum sample of a human as indicative of sepsis or septic shock in the human, comprising detecting protein ESM-1 in the sample from the human with the kit of claim 3, determining a plasma or serum concentration of protein ESM-1 in the sample, and comparing the plasma or serum concentration of protein ESM-1 to an ESM-1 concentration indicative of lack of sepsis or septic shock to determine if the ESM-1 concentration is elevated and indicative of sepsis or septic shock in the human.

15. The method of claim 14, wherein the elevated levels of protein ESM-1 indicative of sepsis or septic shock comprise at least 2.5 ng ESM-1 per mL of plasma or serum.

16. The method of claim 14, wherein the elevated levels of protein ESM-1 indicative of sepsis or septic shock comprise at least 4.5 ng ESM-1 per mL of plasma or serum.

17. The method of claim 14, wherein the elevated levels of protein ESM-1 indicative of sepsis or septic shock comprise at least 10.0 ng ESM-1 per mL of plasma or serum.

* * * * *

UNITED STATES PATENT AND TRADEMARK OFFICE
CERTIFICATE OF CORRECTION

| | |
|---|---|
| PATENT NO. | : 7,473,564 B2 |
| APPLICATION NO. | : 10/416204 |
| DATED | : January 6, 2009 |
| INVENTOR(S) | : Philipp Lassalle et al. |

Page 1 of 1

It is certified that error appears in the above-identified patent and that said Letters Patent is hereby corrected as shown below:

In claim 9, column 25, line 12, "1-2572, or" should read --I-2572, or--.

Signed and Sealed this

Tenth Day of March, 2009

JOHN DOLL
*Acting Director of the United States Patent and Trademark Office*